United States Patent
Perlin et al.

(10) Patent No.: US 7,488,072 B2
(45) Date of Patent: Feb. 10, 2009

(54) EYE TRACKED FOVEAL DISPLAY BY CONTROLLED ILLUMINATION

(75) Inventors: Kenneth Perlin, New York, NY (US); Joel S. Kollin, Brooklyn, NY (US)

(73) Assignee: New York University, New York, NY (US)

(*) Notice: Subject to any disclaimer, the term of this patent is extended or adjusted under 35 U.S.C. 154(b) by 424 days.

(21) Appl. No.: 11/001,206

(22) Filed: Dec. 1, 2004

(65) Prior Publication Data

US 2005/0185281 A1    Aug. 25, 2005

Related U.S. Application Data

(60) Provisional application No. 60/527,066, filed on Dec. 4, 2003.

(51) Int. Cl.
*A61B 3/14* (2006.01)
*A61B 3/10* (2006.01)

(52) U.S. Cl. .................................. 351/209; 351/211

(58) Field of Classification Search ................. 351/209, 351/211

See application file for complete search history.

(56) References Cited

U.S. PATENT DOCUMENTS

| | | | | | |
|---|---|---|---|---|---|
| 4,348,186 | A | * | 9/1982 | Harvey et al. ................. | 434/44 |
| 5,242,306 | A | * | 9/1993 | Fisher .......................... | 434/44 |
| 5,326,266 | A | * | 7/1994 | Fisher et al. .................. | 434/44 |
| 5,341,181 | A | * | 8/1994 | Godard ........................ | 351/210 |
| 5,980,044 | A | * | 11/1999 | Cannon et al. ................ | 353/30 |
| 6,351,335 | B1 | * | 2/2002 | Perlin ........................ | 359/618 |

* cited by examiner

*Primary Examiner*—Jordan M. Schwartz
*Assistant Examiner*—James C Jones
(74) *Attorney, Agent, or Firm*—Ansel M. Schwartz

(57) ABSTRACT

An apparatus for viewing includes a screen. The apparatus includes means for detecting a fixation point of a viewer's eyes on an image on the screen. The apparatus includes means for displaying a foveal inset image on the image on the screen about the fixation point so a viewer's fovea sees the foveal image while the rest of the eye sees the image. A method for viewing. The method includes the steps of detecting a fixation point of a viewer's eyes on an image on a screen. There is the step of displaying a foveal inset image on the image on the screen about the fixation point so the viewers fovea sees the foveal image while the rest of the eye sees the image.

42 Claims, 1 Drawing Sheet

SCHEMATIC DIAGRAM OF FOVEAL DISPLAY SYSTEM

LENS ARRAY ARRANGEMENT

SCHEMATIC DIAGRAM OF FOVEAL DISPLAY SYSTEM

EYE TRACKED FOVEAL DISPLAY BY CONTROLLED ILLUMINATION

This application claims the benefit of U.S. Provisional Application No. 60/527,066 filed Dec. 4, 2003.

FIELD OF THE INVENTION

The present invention is related to a viewing apparatus. More specifically, the present invention is related to a viewing apparatus which displays a foveal inset image on the image on the screen about the fixation point so a viewer's fovea sees the foveal image while the rest of the eye sees the image.

BACKGROUND OF THE INVENTION

The human eye has a high resolution area called the fovea, which is responsible for the perception of color and fine detail using specialized retinal receptors called cones. The foveal region subtends a visual angle of about a degree of arc. Our perception of the world is therefore time-multiplexed, in that we scan this one degree patch around to fill in the details in which we are interested, and assume that these details don't change while we aren't actively perceiving them with our fovea. Our non-foveal receptors (rods) can detect movement very well; they function to guide our eyes so we can more accurately perceive anything which may have changed since we last looked at it with our fovea.

Because the foveal region is so narrow, and the highest resolution displays are so expensive, many people have speculated about and experimented with displays which attempt to present a high resolution "inset" image which can move inside of a lower resolution "surround" image. Ideally, this high-resolution inset would perfectly follow the movement of the eye so that fovea always perceives it; the image shown by the inset would change to match its current position so the fovea can see the correct image for its position. The lower resolution surround image would either be dimmed or blocked for the area of the surround which is temporarily used for the foveal inset, so as not to distract from it.

There are several technical challenges in producing such a foveal display system. The system must accurately perceive where the viewer is looking, it must compute the correct foveal image for the foveal position, and last but not least, it must move the foveal image to the correct position fast enough for the system to be useful. Faster graphics engines and better gaze tracking systems now available make the first two problems tractable. Using a mechanical means (such as a mirror) to move the foveal inset in a projection system may be feasible with the fastest galvanometers available, but this is expensive and likely to be troublesome given the time response needed.

SUMMARY OF THE INVENTION

The present invention pertains to an apparatus for viewing. The apparatus comprises a screen. The apparatus comprises means for detecting a fixation point of a viewer's eyes on an image on the screen. The apparatus comprises means for displaying a foveal inset image on the image on the screen about the fixation point so a viewer's fovea sees the foveal image while the rest of the eye sees the image.

The present invention pertains to a method for viewing. The method comprises the steps of detecting a fixation point of a viewer's eyes on an image on a screen. There is the step of displaying a foveal inset image on the image on the screen about the fixation point so the viewers fovea sees the foveal image while the rest of the eye sees the image.

BRIEF DESCRIPTION OF THE DRAWINGS

In the accompanying drawings, the preferred embodiment of the invention and preferred methods of practicing the invention are illustrated in which.

DETAILED DESCRIPTION

Figure 2:
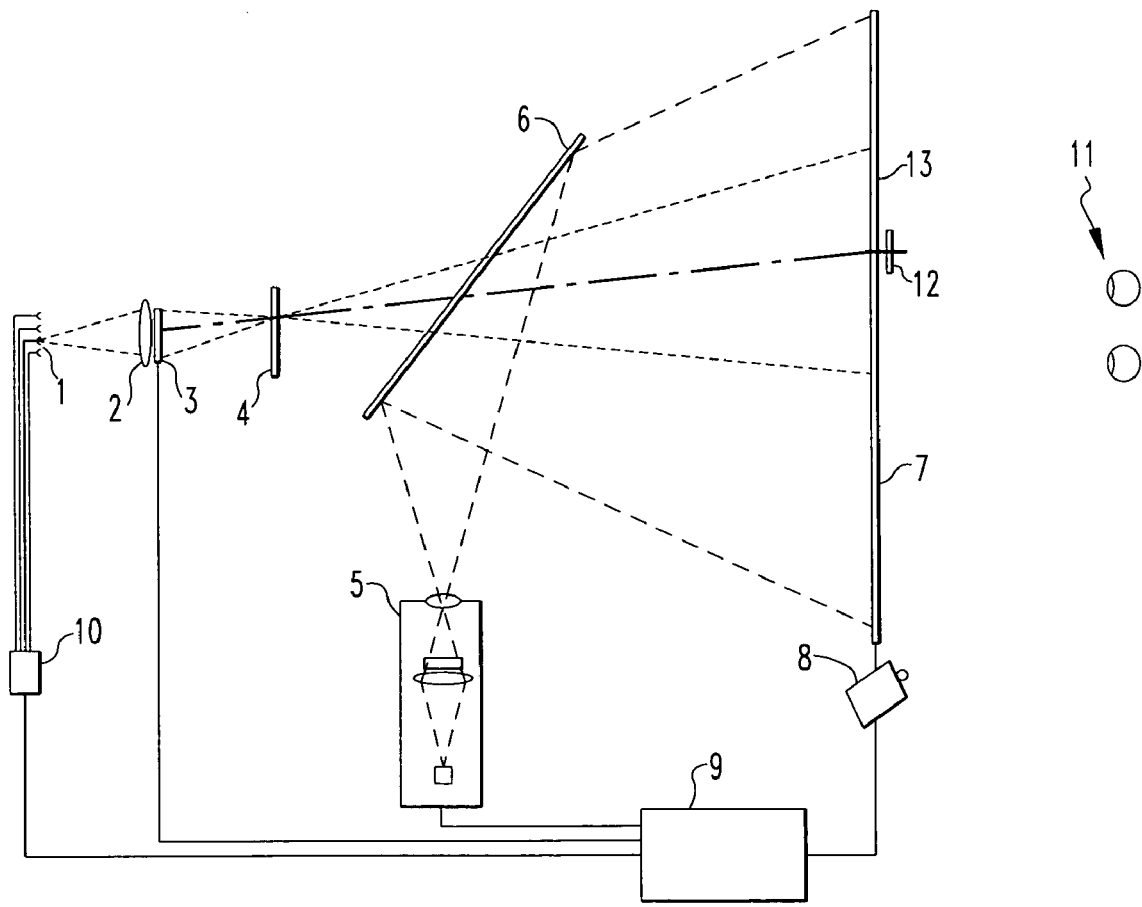
FIG. 2 is a schematic representation of an apparatus of the present invention.

Referring now to the drawings wherein like reference numerals refer to similar or identical parts throughout the several views, and more specifically to FIG. 2 thereof, there is shown an apparatus for viewing. The apparatus comprises a screen. The apparatus comprises means for detecting a fixation point 12 of a viewer's eyes 11 on an image on the screen. The apparatus comprises means for displaying a foveal inset image on the image on the screen about the fixation point 12 so a viewer's fovea sees the foveal image while the rest of the eye sees the image.

Preferably, the displaying means includes a surround image projector 5 which produces the image on the screen. The display means preferably includes a computer 9 in communication with the surround image projector 5 and the detecting means which receives the fixation point 12 and causes the foveal inset image whose center is closest to the fixation point 12 to be displayed on the image on the screen. Preferably, the displaying means includes light sources 1 which produce the foveal inset image at the direction of the computer 9.

The display means preferably includes an illuminating switching system in communication with the light sources 1 and the computer 9 which turns on the light sources 1 at the direction of the computer 9. Preferably, the displaying means includes a condensing lens 2 disposed between the light sources 1 and the screens screen. The displaying means preferably includes an array of projection lenses 4 disposed between the condensing lens 2 and the screen, the condensing lens 2 imaging the light from the light sources 1 into a corresponding lens of the array.

Preferably, the displaying means includes an LCD 3 in communication with the computer 9 which sends an image for the foveal region image to the LCD 3, the LCD 3 disposed between the array and the screen, light from the light sources 1 which is imaged by the condensing lens 2 passes through the LCD 3. The computer 9 preferably causes the surround image projector 5 to black out the region of the image on the screen that corresponds to where the foveal inset image is displayed on the screen. Preferably, the displaying means includes a beam splitter/combiner 6 disposed between the array and the screen through which the foveal region image passes and from which the image from the surround image projector 5 is reflected. The detecting means preferably includes an eye-tracking system 8. Preferably, the light sources 1 are LEDs.

The present invention pertains to a method for viewing. The method comprises the steps of detecting a fixation point 12 of a viewer's eyes 11 on an image on a screen. There is the step of displaying a foveal inset image on the image on the screen about the fixation point 12 so the viewers fovea sees the foveal image while the rest of the eye sees the image.

Preferably, there is the step of blacking out the region of the image on the screen that corresponds to where the foveal inset image is displayed on the screen. There is preferably the step of updating where the foveal inset image is displayed on the screen when the detected fixation point 12 moves closer to a center of a different foveal display region 13. Preferably, the detecting step includes the step of detecting a fixation point 12 of the viewer's eyes 11 looking at the screen with an eye tracking system.

The displaying step preferably includes the step of sending a location of the fixation point 12 to a computer 9. Preferably, there is the step of activating by the computer 9 the foveal display region 13 whose center is the closest to the fixation point 12. There is preferably the step of directing by the computer 9 an illuminator switching system 10 to turn on an LED which is imaged by a condensing lens 2 onto a corresponding lens of an array of projection lenses 4. Preferably, there is the step of sending an appropriate image for the foveal region to an LCD 3.

In the operation of the preferred embodiment, a projection display "moves" the image by changing the illumination of a spatial light modulator (cf LCD panel). This can be accomplished by sharing the same LCD 3 panel as a common element of different optical systems—each of which has a different light source (LED or lamp) and corresponding projection lens. As shown in FIG. 2, each optical path forms a projected image of the LCD 3 at different position. If the lens pitch is half the width of the LCD 3 panel, the images of adjacent paths would overlap by about 50%. In this embodiment, only one LED would be illuminated at a time—the one corresponding to the closest image to the foveal region. Allowing the areas to overlap means that perfect gaze tracking is not required, and dithering between adjacent regions at the boundary can be reduced.

Figure 1:
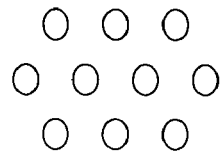
FIG. 1 shows a lens array arrangement.

Bear in mind that an actual system would presumably use a 2D array of LEDs and projection lenses to allow the foveal inset to "move" vertically as well as horizontally. For example, in the initial prototype, 10 lenses are used in a "honeycomb" format as shown in FIG. 1.

Given a LCD resolution of 1280×1024, this would give an effective resolution of:

x3=3840 by 3072

The effective resolution of the system, which determines the field of view seen by an observer at a distance which takes full advantage of viewer's foveal resolution, is entirely a function of the LCD 3 resolution and the number of lenses. If a 4,5,4 lens array is used (for wide-screen) the final resolution would by 4x and 3y, or 5120 by 3072. Given a simplified foveal acuity model of 60 pixels per degree, we can obtain an optimal field of view of (5120/60)×(3072/60) or about 85 degrees horizontal by 51 degrees vertical.

It should also be noted that the inevitable distortions will change with the differing optical paths, and needs to be compensated for in a calibration step. Also, the lower resolution surround image can be provided by a separate optical system which might be an identical LCD 3 with a shorter focal length lens. The surround and foveal paths could be combined by a beamsplitter or might just overlap at the projection surface with appropriate keystone correction.

The surround image can be dynamically updated to blank out the area of the surround with edge blending. It will be less necessary to make the blending "perfect" than to eliminate any high spatial frequency components (sharp edges) or rapid flickering at the boundary between the inset and surround images, which might be picked up by the viewers' peripheral vision. One method to minimize this transition is to selectively decimate and low-pass filter the part of the inset window which is furthest away from the fixation point 12, so that it matches the lower resolution of the surround window.

Details about the optical system are as follows:

The overlap (at a reasonable projection distance >> than the projection lens focal length) is entirely a function of the projection lens array pitch to LCD 3 size. If the lens pitch is half the LCD 3 diameter, 50% overlap is achieved, enabling the foveal region to be centered at a point close to fixation point 12. Thus, the lenses must be small enough to fit this spacing. The light from each LED is imaged into the corresponding projection lens by the condenser lens just upstream of the LCD 3. Each LED image must not bleed into adjacent lenses or crosstalk will occur. The condenser lens must therefore match the etandue (size*angular extent) of the LEDs and the projection lenses, and the size of the LCD 3. An ideal LED would not only be bright but have the narrowest possible angular spread, so that as much light a possible is imaged by the condenser onto the correct projection lens.

PARTS LIST

1. Light sources (LEDs)
2. Condensing Lens
3. Foveal image LCD
4. Array of Projection Lenses
5. Surround Image Projector
6. Beam Splitter/Combiner
7. (Surround image region of) Projection Screen
8. Eye-tracking system
9. Computer
10. Illuminator Switching system
11. Viewer's eyes
12. Fixation point of viewer
13. Foveal display region of projection screen Operational Description:

Overview:

Eye tracking system 8 detects the fixation point 12 of the viewer's eyes 11 looking at the screen, and sends the location of the fixation point 12 to computer 9. The foveal display region 13 whose center is the closest to the fixation point 12 is activated by the computer 9, which directs the illuminator switching system 10 to turn on the LED which is imaged by condensing lens 2 onto the corresponding lens of array 4. Simultaneously, the computer 9 sends the appropriate image for the foveal region to LCD 3 and blacks out the corresponding region projected by surround image projector 5. The viewer's fovea sees the foveal image 13 while the rest of the eye sees the surround image 7, and system updates when the detected fixation point 12 moves closer the center of a different foveal display region 13.

Detailed:

For the following, we refer to the coordinates of the image as x and y, the coordinates of the center of each foveal inset image (i,j) as xi and yj (where i and j are the column and row of a given inset image). I and j also refer to the corresponding LED and projection lens elements which produce foveal inset image (i,j)

1. Eye tracking system 8 detects the fixation point 12 of the viewer's eyes 11 looking at the screen.
2. The coordinates (xe,ye) of the fixation point 12 are sent to the computer 9.
3. The computer 9 determines which foveal inset image is closest to the fixation point 12 by determining which values of i and j yield the minimum result for $(distance2)=(xi-xe)2+(yi-ye)2$
4a. The foveal inset image 13 whose center is the closest to the fixation point 12 is activated by the computer 9, which directs the illuminator switching system 10 to turn on the LED (−i,−j) which is imaged by condensing lens 2 onto the corresponding lens (i,j) of array 4.

4b. At approximately the same time as 4a, the computer 9 sends the high resolution foveal inset image for the foveal region to LCD 3 and blacks out the corresponding region projected by surround image projector 5. For example, in a display which uses a projection lens array pitch of half the LCD size along each axis, there is exactly 50% overlap. Therefore the blacked-out region is defined as $(x_i-(x/(i+1)))$ to $(x_i+(x/(i+1)))$ horizontally, and $(y_j-(y/(j+1)))$ to $(y_j+(y/(j+1)))$ vertically.

5. The viewer's fovea and nearby areas of the retina sees the foveal image 13 while the rest of the retina sees the surround image 7.

6. The system updates when the detected fixation point 12 moves closer to the center of a different foveal display region 13 as determined by the method of step 3.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

References, all of which are incorporated by reference herein:

U.S. Pat. No. 4,479,784 Eye line-of-sight responsive wide angle visual system (Mallinson et al.)

U.S. Pat. No. 6,351,335 Extremely high resolution foveated display (Perlin)

What is claimed is:

1. An apparatus for viewing comprising:
   a screen;
   means for detecting a fixation point of a viewer's eyes on an image on the screen; and
   means for displaying a foveal inset image on the image on the screen about the fixation point so a viewer's fovea sees the foveal image while the rest of the eye sees the image, the displaying means includes a plurality of light sources for displaying the foveal inset image, the light sources being illuminated at different times to move the foveal inset image at least one of vertically or horizontally.

2. An apparatus as described in claim 1 wherein the light sources are illuminated at different times to move the foveal image vertically and horizontally.

3. An apparatus as described in claim 2 wherein the displaying means includes a surround image projector which produces the image on the screen.

4. An apparatus as described in claim 3 wherein the displaying means includes a computer in communication with the surround image projector and the detecting means which receives the fixation point and causes the foveal inset image whose center is closest to the fixation point to be displayed on the image on the screen.

5. An apparatus as described in claim 4 wherein the light sources which produce the foveal inset image are directed by the computer.

6. An apparatus as described in claim 5 wherein the displaying means includes an illuminating switching system in communication with the light sources and the computer which turns on the light sources at the direction of the computer.

7. An apparatus as described in claim 6 wherein the displaying means includes a condensing lens disposed between the light sources and the screen.

8. An apparatus as described in claim 7 wherein the displaying means includes an array of projection lenses disposed between the condensing lens and the screen, the condensing lens imaging the light from the light sources into a corresponding lens of the array.

9. An apparatus as described in claim 8 wherein the displaying means includes an LCD in communication with the computer which sends an image for the foveal region image to the LCD, the LCD disposed between the array and the screen, light from the light sources which is imaged by the condensing lens passes through the LCD.

10. An apparatus as described in claim 9 wherein the computer causes the surround image projector to black out the region of the image on the screen that corresponds to where the foveal inset image is displayed on the screen.

11. An apparatus as described in claim 10 wherein the displaying means includes a beam splitter/combiner disposed between the array and the screen through which the foveal region image passes and from which the image from the surround image projector is reflected.

12. An apparatus as described in claim 11 wherein the detecting means includes an eye-tracking system.

13. An apparatus as described in claim 12 wherein the light sources are LEDs.

14. A method for viewing comprising the steps of:
   detecting a fixation point of a viewer's eyes on an image on a screen;
   displaying a foveal inset image with a plurality of light sources on the image on the screen about the fixation point so the viewer's fovea sees the foveal image while the rest of the eye sees the image; and
   illuminating the light sources at different times to move the foveal inset image at least one of vertically and horizontally.

15. A method as described in claim 14 wherein the illuminating step includes the step of illuminating the light sources at different times to move the foveal inset image vertically and horizontally.

16. A method as described in claim 15 including the step of blacking out the region of the image on the screen that corresponds to where the foveal inset image is displayed on the screen.

17. A method as described in claim 16 including the step of updating where the foveal inset image is displayed on the screen when the detected fixation point moves closer to a center of a different foveal display region.

18. A method as described in claim 17 wherein the detecting step includes the step of detecting a fixation point of the viewer's eyes looking at the screen with an eye tracking system.

19. A method as described in claim 18 wherein the displaying step preferably includes the step of sending a location of the fixation point to a computer.

20. A method as described in claim 19 including the step of activating by the computer the foveal display region whose center is the closest to the fixation point.

21. A method as described in claim 20 including the step of directing by the computer an illuminator switching system to turn on an LED which is imaged by a condensing lens onto a corresponding lens of an array of projection lenses.

22. A method as described in claim 21 including the step of sending an appropriate image for the foveal region to an LCD.

23. A computer accessible medium containing instructions which, when executed by a processor, instruct the processor to perform the following steps for displaying:
   receiving a fixation point of a viewer's eye on an image;
   generating a foveal inset image;

displaying the foveal inset image on the image in correspondence with the fixation point with a plurality of light sources so the viewer's fovea sees the foveal inset image while the rest of the eye sees the image; and illuminating the light sources at different times to move the foveal inset image at least one of vertically and horizontally.

24. The computer accessible medium of claim 23 wherein the illuminating step includes the step of illuminating the light sources at different times to move the foveal inset image vertically and horizontally.

25. The computer accessible medium of claim 24 wherein the generating step selects a foveal inset image closest to the fixation point.

26. The computer accessible medium of claim 24 wherein the instructions, when executed by a processor, cause a surround image to be displayed.

27. The computer accessible medium of claim 26 wherein the instructions, when executed by a processor, cause a portion of the surround image to be blacked out corresponding to the selected foveal inset image.

28. The computer accessible medium of claim 23 wherein the instructions when executed by a processor cause one or more of the light sources to illuminate the selected foveal inset image.

29. The computer accessible medium of claim 28 wherein the illuminating step illuminates at least one lens among a plurality of lenses each corresponding to a foveal inset image.

30. An apparatus for viewing by a viewer comprising:
a first displayer for displaying a first image; and
a second displayer for displaying a second image wherein the first image and second image have different optical paths and the second displayer displays the second image so as to be seen by the viewer's fovea, the second displayer having a plurality of light sources, the light sources being illuminated at different times to move the foveal inset image vertically and horizontally.

31. An apparatus as described in claim 30 wherein the light sources are illuminated at different times to move the foveal inset image vertically and horizontally.

32. An apparatus as described in claim 31 wherein the viewer's fovea and nearby areas of the retina see the second image while the rest of the retina sees the first image.

33. An apparatus as described in claim 31 wherein the second image has a higher resolution than the first image.

34. An apparatus as described in claim 30 wherein the second image is inset in the first image near the fixation point of the viewer's eyes.

35. An apparatus as described in claim 30 wherein the area corresponding to the second image is blacked out of the first image.

36. An apparatus as described in claim 30 including a controllable light source which produces the second image by illuminating at least one of a plurality of inset images.

37. An apparatus as described in claim 1 wherein the plurality of light sources include an LED.

38. An apparatus as described in claim 4 wherein the computer causes the surround image projector to black out the region of the image on the screen that corresponds to where the foveal inset image is displayed on the screen.

39. An apparatus for viewing comprising:
a screen;
an eye tracking system for detecting a fixation point of a viewer's eyes on an image on the screen; and
a displayer for displaying a foveal inset image on the image on the screen about the fixation point so a viewer's fovea sees the foveal image while the rest of the eye sees the image, the displaying means includes a plurality of light sources for displaying the foveal inset image the light sources being illuminated at different times to move the foveal inset image at least one of vertically and horizontally.

40. A method as described in claim 14 wherein the displaying step includes the step of displaying the foveal inset image with a plurality of LEDs.

41. An apparatus as described in claim 31 wherein there is edge blending of the first image by the first displayer so there are no sharp edges that appear where the second image transitions with the first image.

42. An apparatus as described in claim 39 wherein the light sources are illuminated at different times to move the foveal inset image vertically and horizontally.

* * * * *